United States Patent [19]

Plamondon

[11] Patent Number: 4,976,969

[45] Date of Patent: Dec. 11, 1990

[54] OPHTHALMIC SOLUTION COMPRISING IODINE-POLYVINYLPYRROLIDONE COMPLEX

[76] Inventor: Marc Plamondon, 1325, Ave des Gouverneurs, Sillery, Quebec, Canada, G1T 2G4

[21] Appl. No.: 269,224

[22] Filed: Nov. 9, 1988

[30] Foreign Application Priority Data

Nov. 10, 1987 [CA] Canada ................................ 551522

[51] Int. Cl.$^5$ ...................... A61K 33/18; A61K 31/79
[52] U.S. Cl. ...................................... 424/672; 424/80; 514/839; 514/840; 514/912; 514/915
[58] Field of Search ................................ 424/672, 80; 514/912–915, 839, 840

[56] References Cited

U.S. PATENT DOCUMENTS

| | | | |
|---|---|---|---|
| 3,911,107 | 10/1975 | Krezanoski | 424/672 |
| 4,031,209 | 6/1977 | Krezanoski | 424/672 |
| 4,364,929 | 12/1982 | Sasmor et al. | 424/672 |
| 4,401,651 | 8/1983 | Knutson | 424/80 |
| 4,452,780 | 6/1984 | Ecanow | 424/672 |
| 4,525,346 | 6/1985 | Stark | 424/80 |
| 4,581,226 | 4/1986 | Dillon | 424/49 |
| 4,708,873 | 11/1987 | Schulte | 514/947 |
| 4,713,446 | 12/1987 | DeVore et al. | 514/912 |
| 4,851,513 | 7/1989 | DeVore et al. | 514/912 |
| 4,873,265 | 10/1989 | Blackman | 514/651 |

OTHER PUBLICATIONS

York et al., C.A. 110 #165620e(1989) of J. Ocul. Pharmacol, 4(4):351-8(1988).
Roberts et al., C.A. 105 #17912h(1986).
Kim et al., C.A. 103 #189257y(1985).
Wille et al., C.A. 98 #137590k(1983).
Clough et al., C.A. 96 #149212k(1982).
Andrews et al., C.A. 88 #197613y(1978).
White et al., C.A. 78 #106019p(1973).

*Primary Examiner*—Shep K. Rose
*Attorney, Agent, or Firm*—Dressler, Goldsmith, Shore, Sutker & Milnamow, Ltd.

[57] ABSTRACT

An ophthalmic solution comprising 0.1 to 0.9 % volume of povidone iodine in association with a suitable ophthalmic carrier. The solution is useful in treating various ophthalmic disorders such as follicular conjunctivitis and giant papillary conjunctivitis resulting from reaction to contact lenses, cosmetics and allergies among others. It is also useful in the treatment of ocular dryness resulting from post menopausal stage and from Sjögren's disease.

1 Claim, No Drawings

OPHTHALMIC SOLUTION COMPRISING IODINE-POLYVINYLPYRROLIDONE COMPLEX

BACKGROUND OF THE INVENTION

Conjunctivitis is an ophthalmologic disorder mainly characterized by inflammation of the conjunctiva. Conjunctivitis is usually caused by viruses, allergy or bacteria, although conjunctival irritation from wind, dust, smoke, and other types of air pollution is also quite frequent. This disorder may also accompany the common cold, exanthems, and corneal irritation due to the intense light of electric arcs, sun lamps, and reflection from snow. In the case of bacterial infections, antibiotic ointments are usually applied. However, if allergy is likely on the basis of history and if there is lack of response to antibiotic therapy, topical corticosteroid therapy can be initiated.

Vernal conjunctivitis is a bilateral chronic conjunctivitis, probably allergic in origin, usually recuring in the spring and lasting through the summer. It is often associated to intense itching, lacrimation, photophobia, conjunctival injection, and a tenacious mucoid discharge containing numerous eozinophiles. Although these symptoms usually disappear during the cold months and become milder over the years, the granulations which appear in the upper lids during spring and summer often persist for life. Again, applications of topical corticosteroids are usually beneficial but must often be supplemented by small oral doses. Furthermore, topical applications of steroids for long periods of time are usually not recommended and intraocular pressure must in these cases be carefully monitored.

Another frequent form of conjunctivitis, keratoconjunctivitis sicca, is characterized by a chronic, bilateral dryness of the conjunctiva and sclera leading to dessication of the ocular surface. This type of conjunctivitis occurs more commonly in adult women. It is initially characterized by reduction of tear production leading to burning and irritation as well as pain in the fornices during the night. This proceeds to photophobia and blepharospasms as the corneal epithelium develops scattered cellular loss which is termed superficial karatitis. In its advanced stages, karatinization of the ocular surface occurs and is frequently associated with loss of the normal configuration of the conjunctival fornices.

Various degrees of follicular conjunctivitis may be observed. Thus, depending on the amount of follicles detected on the conjunctival side of the eyelids tarsus, especially the superior eyelid, various grades of conjunctivitis are diagnosed. In most cases, this type of follicular reaction is due to "hay fever" and contact lenses and there is not adequate efficient local treatment for this affection.

In the latent stage or grade I, 10 to 20 microfollicles may be localized at the angles of the eversed superior tarsus. A smaller amount of microfollicles can also be found on the edge of the inferior eversed tarsus. In the event smaller overall amounts of microfollicles are observed, the condition can be described as a fraction of grade I, such as grade 0.5 or grade 0.25. At this stage, no inflammation is noted and no pain is felt by the patient.

Grade II is characterized by the presence of microfollicles on half of the height of the tarsal plate. Oedema of the tarsal plate may also be present. It is usually characterized by a dull, satin aspect of the tarsus, an absence of lubrication and very often by redness caused by inflammatory hyperhemia.

Finally, grade III corresponds to a stage where most of the tarsal plate is covered by microfollicles, accompanied by oedema and redness. At this stage, the presence of a few follicles as well as redness may be noted on the inferior tarsus. In grade IV, large follicles forming folds as well as oedema, redness and secretions may be seen on both tarsus as well as on the bulbous conjunctiva.

Although some relief medication is currently available, an effective chemical treatment for conjunctivitis is still being sought.

Therefore, effective medication useful in controlling, diminishing or even eliminating the various forms of follicular conjunctivitis as well as ocular dryness would be highly desirable.

SUMMARY OF THE INVENTION

In accordance with the present invention, there is provided an ophthalmic solution comprising from 0.1 to 0.9% volume of povidone iodine in association with a suitable ophthalmic carrier. This solution is useful in treating various forms of ophthalmic disorders such as follicular conjunctivitis and giant papillary conjunctivitis resulting from reactions to contact lenses, cosmetics and allergies among others. The solution is also useful for the treatment of ocular dryness resulting from post menopausal stage and from Sjögren's disease. The ophthalmic solution of the present invention may also comprise other eye-treating medication such as antibiotics and corticosteroids.

DETAILED DESCRIPTION OF THE INVENTION

The present invention relates to an ophthalmic solution comprising povidone iodine.

The solution is to be used for the treatment of various ophthalmic disorders. Povidone iodine is an iodine complex of 1-vinyl-2-pyrrolidone. It is a known topical antiinfective and it has been used mainly as a disinfectant solution and in wound-healing compositions.

Povidone iodine (PVP-I) is commercially available in various forms such as antiseptic gauze pads, solution, solution swab aid, aerosol spray, surgical scrub, douche, vaginal gel, skin cleanser, ointment, microbicidal bath, and perineal wash among others. However, the most convenient form of povidone iodine to be used in the context of the present invention is sold by Purdue Frederick under the trade name Betadine $^O$ in the form of ointment or solution which usually contains approximately 1% volume of povidone iodine. The carriers used in these solutions are suitable for the purposes of the present invention although the addition of further carriers may be contemplated. Other suitable carriers such as commercially available natural tears and the like are also suitable. It will be understood that the Betadine $^O$ solution or ointment will have to be diluted since the optimal povidone iodine concentrations to be employed as an ophthalmic solution are lower than 1%. The concentration of povidone iodine to be used in the ophthalmic solution of the present invention may vary from 0.1 to 0.9% volume. It is to be noted that the desired ophthalmic solution may also contain a suitable ophthalmic carrier such as hydroxyethyl cellulose, methylcellulose or polyvinyl alcohol as well as any suitable preservative which will be included in order to prevent bacterial growth. It may also contain an antihistamine agent as well as a vasoconstrictor.

The methylcellulose used in the ophthalmic solution of the present invention is a methyl ether of cellulose, produced by treating cellulose with a suitable alkali and by methylating the alkali cellulose with methyl chloride. The methyl cellulose used in the compositions described herein is sold by Alcon under the trade mark Tears Naturale. It is to be understood, however, that the invention is not limited to the use of any particular methylcellulose and that any equivalent methylcellulose of pharmaceutical grade can be used to achieve similar results.

The polyvinyl alcohol which may be used in the ophthalmic solution of the present invention may be either fully hydrolyzed or partially hydrolyzed material having average molecular weight ranging from 2000 to 125,000. It is preferred, however, to use polyvinyl alcohol having an average molecular weight of about 100,000 to 125,000. The polyvinyl alcohol which can be found in the composition described herein is sold by Coopervision under the trade mark Hypotears. However, the invention is not limited to a use of any specific polyvinyl alcohol and any equivalent may be used.

Finally, the ophthalmic solutions of the present invention may contain an additional preservative to prevent bacterial growth. Pharmaceutically acceptable preservatives such as phenylmercuric nitrate, thimerosal, and benzalkonium chloride may be used in concentrations varying between 0.001 to 0.002% by weight.

It will be readily understood by those skilled in the art that the concentration of the various ingredients contained in the ophthalmic solution disclosed herein will vary depending on the nature of the affection to be treated.

For example, when it is desired to treat a reaction to contact lenses, an ophthalmic solution containing between 0.4 and 0.9% volume of povidone iodine in a carrier such as methylcellulose or polyvinyl alcohol, from 30 to 60% v/v of commercial natural tears and from 0.2 to 0.5% v/v of a preservative such as chlorbutanol may be administered. The optimal dosage will vary between 1 and 3 drops a day during the active treatment period. Once the treatment has been achieved, it might be necessary for the patient to maintain minimal use of the solution if contact lenses are to be worn again. A povidone iodine concentration of 0.45% volume and a 56% v/v natural tears concentration the natural solution being sold under the name Tears Naturale and comprising dextran 70 (0.1%) and hydropropyl methylcelluloce (0.3%) are the preferred concentrations to be used for treatment of reaction to contact lenses.

For the treatment of ocular dryness and minor reactions to contact lenses, a solution containing between 0.1 and 0.4% volume of povidone iodine in a carrier selected from methylcellulose or polyvinyl alcohol among others, between 30 and 60% v/v of commercial natural tears and from 0.2 to 0.4% v/v of a suitable preservative, for example Tears Naturale and Hypotears. Again the optimal dosage will vary between 1 and 3 drops a day, 1 drop every 12 hours being the preferred amount.

In the case of severe allergy reactions such as hay fever, the use of an ophthalmic solution containing povidone iodine as well as vasoconstrictor and antihistaminic agents should be employed. Thus, such an ophthalmic solution will contain between 0.4 and 0.9% volume of povidone iodine in a suitable carrier such as the carriers mentioned above, from 30 to 60% v/v of an ophthalmic solution containing between 20 and 40% v/v of a vasoconstrictor such as naphazoline HCL 0.025 and from 0.2 to 0.4% v/v of an antihistaminic agent selected from pheniramine malleate, and from 0.01 to 0.02% v/v of a preservative such as benzalkonium chloride. Preferably, an ophthalmic solution containing 0.45% volume of povidone iodine in a methylcellulose carrier, 55% v/v of a solution sold under the name Naphcon A and containing 0.025% v/v of the vasoconstrictor naphazoline HCL and 0.3% v/v of the antihistaminic pheniramine malleate represents the best mode of use.

The quantity of solution to be administered daily, which may vary from 1 to 3 drops, will depend mainly on the severity of the allergy reaction.

Finally, in more severe cases of conjunctivitis, treatment with solutions described earlier accompanied by local administrations of either steroids or antibiotics, or both, is indicated. Among the combined steroids-antibiotics that may be used, there may be mentioned Cetapred ®, metimyd, and the like. Chloromycetin ®, garamycin and the like are the preferred antibiotics.

Table I summarizes the treatment results obtained on patients suffering from various grades of conjunctivitis resulting from either reaction to contact lenses (cont. lenses) allergy to cosmetics (aller. (cosm.)), the common cold, allergy to cats (aller. (cats)) or scrofula (scrof.) and calculus (calc.)

TABLE I

Treatment of various grades of conjuctivitis using povidone-iodine solutions

| CONJUNCTIVITIS | | Concentration | Duration |
|---|---|---|---|
| Cause | Before treatm. | After treatm. | povidone-iodine (% PVP-I) | treatm. (weeks) |
| Cont. lenses | 2 | 0.0 | 0.45 | 1 |
| Cont. lenses | 4 | 0.0 | 0.45 | 4 |
| Cont. lenses | 3 | 0.0 | 0.45 | 3 |
| Cont. lenses | 3 | 0.0 | 0.45 | 2 |
| Cont. lenses | 3 | 0.5 | 0.45 | 1 |
| Cont. lenses | 3 | 0.5 | 0.45 | 1 |
| Cont. lenses | 3 | 0.5 | 0.45 | 3 |
| Cont. lenses | 2 | 0.5 | 0.45 | 2 |
| Cont. lenses | 2 | 0.5 | 0.45 | 3 |
| Cont. lenses | 2 | 0.5 | 0.45 | 2 |
| Cont. lenses | 3 | 0.5 | 0.45 | 4 |
| Cont. lenses | 2 | 1.0 | 0.90 | 2 |
| Cont. lenses | 3 | 1.0 | 0.45 | 2 |
| Cont. lenses | 3 | 0.5 | 0.45 | 2 |
| Cont. lenses | 4 | 1.0 | 0.45 | 3 |
| Cont. lenses | 3 | 0.5 | 0.45 | 2 |
| Cont. lenses | 3 | 1.0 | 0.90 | 2 |
| Cont. lenses | 3 | 1.0 | 0.90 | 2 |
| Cont. lenses | 3 | 1.0 | 0.45 | 2 |
| Cont. lenses | 3 | 1.0 | 0.45 | 4 |
| Cont. lenses | 4 | 0.5 | 0.45 | 4 |
| Cont. lenses | 2 | 0.0 | 0.45 | 2 |
| Cont. lenses | 3 | 0.0 | 0.45 | 2 |
| Cont. lenses | 2 | 0.5 | 0.45 | 5 |
| Cont. lenses | 2 | 0.5 | 0.45 | 2 |
| Cont. lenses | 2 | 0.5 | 0.45 | 2 |
| Cont. lenses | 2 | 0.5 | 0.45 | 2 |
| Cont. lenses | 1 | 0.5 | 0.45 | 1 |
| Cont. lenses | 4 | 1.0 | 0.45 | 2 |
| Cont. lenses | 2 | 1.0 | 0.45 | 2 |
| Cont. lenses | 3 | 0.5 | 0.45 | 2 |
| Cont. lenses | 3 | 0.5 | 0.45 | 4 |
| Cont. lenses | 2 | 0.5 | 0.45 | 2 |
| Cont. lenses | 1 | 1.0 | 1.00 | 2 |
| Cont. lenses | 3 | 1.0 | 0.45 | 2 |
| Cont. lenses | 2 | 0.5 | 0.45 | 2 |
| Cont. lenses | 2 | 0.5 | 0.45 | 2 |
| Cont. lenses | 2 | 0.5 | 0.45 | 1 |
| Cont. lenses | 2 | 0.5 | 0.45 | 1 |

TABLE I-continued

Treatment of various grades of conjuctivitis using povidone-iodine solutions

| Cause | CONJUNCTIVITIS Before treatm. | CONJUNCTIVITIS After treatm. | Concentration povidone-iodine (% PVP-I) | Duration treatm. (weeks) |
| --- | --- | --- | --- | --- |
| Cont. lenses | 2 | 0.5 | 0.90 + 0.45 | 1 |
| Cold | 2 | 0.0 | 0.45 | 4 |
| Aller. (cosm.) | 4 | 2.0 | 0.45 | 4 |
| Aller. (cats) | 4 | 2 | 0.90 + 0.45 | 2 |
| Scrof. + calc. | 4 | 0.5 | 0.45 | 1 |

It will be noted that even though no noticeable reaction was observed for a small minority of patients, most patients demonstrated very good responses in relatively short periods of time.

What is claimed is:

1. A method for treating allergic follicular conjunctivitis, giant papillary conjunctivitis, vernal conjunctivitis, kerato conjunctivitis sicca, and ocular dryness, which comprises administering a therapeutically effective amount of an ophtalmic solution which comprises about 0.4 to 0.9% of povidone iodine in association with a pharmaceutically acceptable ophtalmic carrier selected from the group consisting of hydroxyethyl cellulose, methylcellulose and polyvinylalcohol.

* * * * *